US006478763B1

United States Patent
Simonsen et al.

(10) Patent No.: US 6,478,763 B1
(45) Date of Patent: Nov. 12, 2002

(54) PACKING DEVICE FOR RETRIEVING A TAMPON PLACED THEREIN

(75) Inventors: Frederick H. Simonsen, Cincinnati, OH (US); Alicia M. Hall, Cincinnati, OH (US); Letha M. Hines, Wyoming, OH (US); Bruce K. Bitowft, Wyoming, OH (US); John T. Milby, Harrison, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/695,544

(22) Filed: Oct. 24, 2000

Related U.S. Application Data

(63) Continuation-in-part of application No. 09/342,409, filed on Jun. 28, 1999.

(51) Int. Cl.[7] ................................................ A61F 13/00
(52) U.S. Cl. .......................................... 602/79; 604/904
(58) Field of Search ................................ 604/358, 904; 206/225, 226, 438, 440, 570, 574, 581; 132/286

(56) References Cited

U.S. PATENT DOCUMENTS

| | | | |
|---|---|---|---|
| 3,092,251 A | 6/1963 | Jaggers | |
| 4,648,513 A | * 3/1987 | Newman | |
| 5,180,059 A | 1/1993 | Shimatani et al. | |
| 5,827,251 A | 10/1998 | Moder et al. | |
| 5,884,771 A | * 3/1999 | McCormick | ................ 206/581 |
| 5,891,127 A | 4/1999 | Moder et al. | |
| 5,964,741 A | 10/1999 | Moder et al. | |
| 5,986,165 A | 11/1999 | Moder et al. | |
| 6,010,001 A | 1/2000 | Osborn, III | |
| 6,045,544 A | 4/2000 | Hershberger et al. | |
| 6,131,736 A | 10/2000 | Farris et al. | |

* cited by examiner

*Primary Examiner*—Michael A. Brown
*Assistant Examiner*—Lalita M Hamilton
(74) *Attorney, Agent, or Firm*—Ingrid N. Hickman

(57) ABSTRACT

An individual package in combination with a hygienic device has a body comprising walls which surround and contain the device within the body; a rupturable seal line running along the axis of at least one side of the body, and an opening member situated on the seal line and extending outward from the body. The hygienic device is positioned within the package. The hygienic device is readily retrievable from the package such that a user neither touches nor contaminates the absorbent portion of the hygienic device with any part of her hand prior to the use and in using the hygienic device. Tampons, interlabial devices, swabs, and bandages are thereby afforded means for sterile usage and subsequent hygienic disposal.

7 Claims, 3 Drawing Sheets

PACKING DEVICE FOR RETRIEVING A TAMPON PLACED THEREIN

This is a continuation-in-part of application Ser. No. 09/342,409, filed on Jun. 28, 1999.

FIELD OF THE INVENTION

This invention relates to a sanitary protection packaging used for retrieving hygienic devices therein and provides full and complete sanitary protection, ease in handling, and discretion in packaging appearance.

BACKGROUND OF THE INVENTION

All manner and variety of absorbent articles configured for the absorption of body fluids such as menses, urine and feces are, of course, are well known. With respect to feminine protection devices, the art has offered two basic types; sanitary napkins have be en developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator," issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices that attempt to merge the structural features of the sanitary napkins and the tampons into a single device have also been proposed. Such hybrid devices are disclosed in U.S. Pat. No. 2,092,346, entitled "Catamenial Pad," issued to Arone on Sep. 7, 1937, and U.S. Pat. No. 3,905,372, entitled "Feminine Hygiene Protective Shield," issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad," issued to Jacks on Dec. 15, 1953, and U.S. Pat. No. 4,631,062, entitled "Labial Sanitary Pad," issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,43,235 issued to Harmon on Jan. 7, 1969, and U.S. Pat. No. 4,595,392 issued to Johnson, et al. on Jun. 17, 1986. A commercially available interlabial device is FRESH 'N FIT® PADETTE® hygienic product that is marketed by Athena Medical Corp. of Portland, Oreg. and described in U.S. Pat. Nos. 3,983,873 and 4,175,561 issued to Hirschman on Oct. 5, 1976 and Nov. 27, 1979, respectively.

Feminine sanitary protection absorbent articles need to be hygienically stored from the time of their manufacture until the article is used. This is a particular concern with respect to maintaining a sanitary environment prior to placement or insertion. That is, a need exists to hygienically store an absorbent article to prevent transferring unsanitary particles to the pudendal or vaginal area.

The packaging for the commercially available FRESH 'N FIT® PADETTE® hygienic product is made from a coated paper sheet that is wrapped around the product and sealed on the transverse ends and along the longitudinal edges. The transverse ends and longitudinal edges of the product are sometimes sealed with an adhesive and are then crimped or knurled together. An example of packaging for a hygienic pad is shown in U.S. Pat. No. 4,743,245 entitled "Labial Sanitary Pad" that issued to F. O. Lassen, et al. on May 10, 1988.

Other packages for sanitary articles are described in U.S. Pat. No. 3,062,371 entitled "Internally Sterile Composite Package" that issued to D. Patience on Nov. 6, 1962 and U.S. Pat. No. 3,698,549 entitled "Packages for Small Articles" that issued to J. A. Glassman on Oct. 17, 1972.

Packages for tampons are described in U.S. Pat. No. 3,135,262 entitled "Tampon" that, issued to W. Kobler, et al. on Jun. 2, 1964 and U.S. Pat. No. 5,180,059 entitled "Package of a Sanitary Tampon" that issued to S. Shimatani and K. Shimatani on Jan. 19, 1993.

One drawback to the prior art is that packages for hygienic products do not provide a means for users to maintain good hygiene when removing the product from the protective package or inserting a hygienic product into the folds of the skin or into the vagina. The lack of hygiene in restrooms, the need to touch the doors of non-hygienic restrooms, and the necessity to touch themselves while inserting the device may result in the possibility of infection. In addition, when inserting the device during menstruation, it is desirable to keep the user's hands free from soiling. Therefore, the consumer needs an individual package that will hygienically protect a hygienic device during its removal from a package and simultaneously during insertion thereof. Also, the prior art system requires the consumer to open the package in a way that is not necessarily intuitive to the consumer.

Although the packages described in the prior art protect the enclosed article, the package does not aid in the hygienic removal, insertion and placement of the hygienic device or provide a barrier to prevent the wearer's hand from touching the product or the wearer's body. Additionally, such packages do not provide a convenient means for users of hygienic products to dispose of the packaging after the product has been used. Conventionally, users would dispose of the packaging by placing the product in her purse; discarding it on the bathroom floor; placing it in a trash receptacle for sanitary products; winding several layers of toilet paper around the tampon and then depositing it into trash cans; or placing the packaging in a trash receptacle outside of the bathroom stall. These disposal practices lead to a wasteful and an unsanitary/unhygienic environment. Some users may attempt to flush packages whether they are or are not designed to be flushed, and regardless of whether they are dispersible in water or biodegradable. Thus, the current method for disposing used feminine care products, in particular tampon applicators and tampons, is very cumbersome, potentially damaging to plumbing systems, and not very hygienic.

Furthermore, the prior art packages fail to provide a sterile environment because they, too, do not seal all parts of the product inside the package that should be protected from contamination or prevent the user from touching parts that should maintain sterility. In addition, conventional packages serve only the function of sealing up of the sanitary tampons, that is, they are merely thrown away giving no additional use once they are opened.

SUMMARY OF THE INVENTION

The present invention encompasses a package for use with a hygienic device having a body comprising walls which surround and contain the device within the body; a rupturable seal line running adjacent to a permanent seal of at least one side of the body, and an opening member situated on the seal line and extending outward from the body. The opening member is suitable for grasping with the fingers. In one embodiment, the package has two opening members situated opposite each other and are on opposite sides of the seal line. In the embodiment, the opening members are each situated along the longitudinal axis of the body and are laterally displaced from the longitudinal center of the body.

In yet another embodiment herein, a kit has a hygienic device, having a grasping member, an absorbent member; a package, having a body with walls which surround and contain the device within the body; sealing means for the body, the sealing means being defined by a rupturable seal line running adjacent to a permanent seal along at least one side of the body, and an opening member attached to the sealing means the opening member extending outward from the body of the package; said hygienic device being situated within the body of the package such that the grasping member of the device is first presented to the user when the sealing means is ruptured. The opening member may be a tab, a loop, or the like.

In another aspect, the invention provides a method for using the kit by opening the package and retrieving the sanitary device therefrom having the steps of:

a) grasping the package in at least one hand;
b) opening the package by pulling the sealing means to reveal the grasping portion of the sanitary contained therein;
c) gripping the grasping portion of the sanitary device; and
d) removing the sanitary device from the package.

The sanitary device encompasses absorbent structures such as tampons, interlabial devices, bandages, surgical swabs, and the like. In addition, the seal line of the package may be re-sealed once the sanitary device is removed from the package, thereby forming a re-sealable package. Furthermore, the sanitary device can be placed back into the re-sealable package after the tampon applicator or the tampon is used, the re-sealable package is re-sealed with the used tampon applicator or tampon being positioned therein. In addition, the sanitary device can be a tampon in combination with an absorbent member.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be clear to those skilled in the art that the various other changes and modifications can be made without departing from the spirit and scope of the invention.

As used herein, the term "hygienic device" refers to a structure such as a sanitary napkin, pantiliner, interlabial device, or an intervaginal device (tampon). Such devices are intended for use in a "hygienic space," i.e., in the wearer's bodily orifices, such as the vagina, in wounds, in contact with the body, and the like. One example of a hygienic device is a tampon and applicator such as tampon device 1 shown in FIG. 1. In some instances, more than half of the entire hygienic device will reside within such hygienic space, in others, substantially the entire hygienic device will reside within such hygienic space of a female wearer during use.

Figure 1:
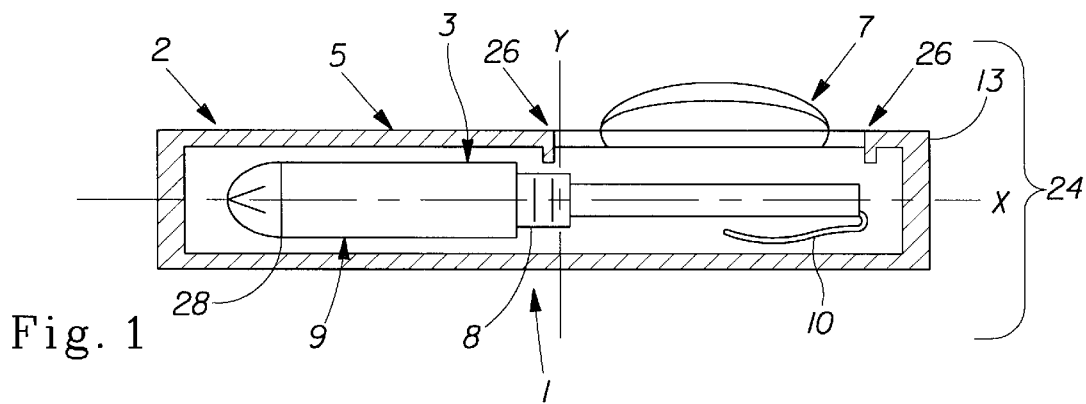
FIG. 1 is a side view of an embodiment of the individual package with offset tabs placed on the end and with the tampon residing therein.

The tampon device 1 can be a tampon in combination with an absorbent member 9. As shown in FIG. 1, the tampon applicator may comprise a pusher tube 27, an absorbent member 9, and the head 28 of the absorbent tampon.

The invention provides a re-sealable feature for packages for a hygienic device. The individual package has a longitudinal axis, a top portion, a bottom portion positioned oppositely to the top portion, an internal first surface and an external second surface. The first surface of the package is also the internal surface thereof and the second surface of the package is also the external surface thereof. In one embodiment herein, the package comprises a single sheet that is folded about the longitudinal axis to form two halves. The package is preferably closed by sealing, for example by permanently sealing of the two ends. At least one side of the package is at least partially sealed non-permanently and may also be re-sealable. One-half of the internal surface of the assembled folded package is connected to and faces the other half of the internal surface of the package.

In another embodiment herein, an individual package for a hygienic device is provided that comprises two sheets of like size and geometry that are attached or secured to one-another, a longitudinal axis, a top portion, a bottom portion positioned oppositely to the top portion, a first surface and a second surface. The first surface of the package is also the internal surface thereof and the second surface of the package is also the external surface thereof.

The invention may provide a kit which has a hygienic device, having a grasping member and an absorbent member; a package, having a body with walls which surround and contain the device within the body; sealing means for the body, the sealing means being defined by a rupturable seal line and a permanent seal line running along the axis of at least one side of the body, and an opening member attached to the sealing means the opening member extending outward from the body of the package; the hygienic device being situated within the body of the package such that only the grasping member of the device is first presented to the user when the sealing means is ruptured. The opening member may be a tab or a loop.

The invention may provide a method for using the kit by opening the package and retrieving the sanitary device therefrom having the steps of:

a) grasping the package in at least one hand;
b) opening the package by pulling the sealing means to reveal only the grasping portion of the sanitary contained therein;
c) gripping the grasping portion of the sanitary device; and removing the sanitary device from the package.

Figure 2:
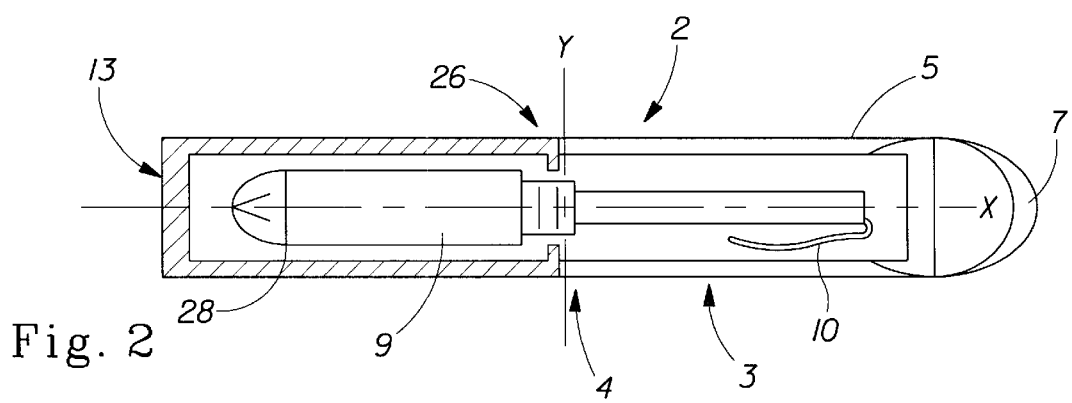
FIG. 2 is a side view of an embodiment of the individual package with tabs placed on the end and with the tampon residing therein.

As can be generally seen from the FIGS. 1–7 the present invention preferably provides a package as well as a kit comprising a hygienic device positioned within the package. As shown in FIGS. 1 and 2, the hygienic device has a lateral x axis X, a longitudinal y axis Y. The hygienic device also preferably has a grasping member 10 for readily retrieving the hygienic device from the package 2. The grasping member 10 prevents the user from either touching or contaminating the hygienic device with any part of her hand. Thus, when the package is opened, the hygienic device is positioned within the package such that the only grasping member 10, which is connected adjacent to the absorbent structure, is accessible after the package opening and is therefore available to be immediately grasped.

A hygienic device is positioned in the package 2. The hygienic device 3 has a longitudinal axis and an absorbent member 10 having a first surface and a second surface. The hygienic device is readily retrievable from the package 2 such that a user neither touches nor contaminates the first surface of the absorbent member 10 of the hygienic device 3 with any part of the hand; this is especially true where a grasping member 10 has been affixed adjacent to the second surface of the hygienic device 3. The hygienic device 3 is preferably positioned within the package such that the hygienic device's 3 first surface of the absorbent member 10 is positioned adjacent to the internal surface of the package 2.

After its use, the hygienic device 3 may be placed back into the package and re-sealed for disposal purposes. At least one side of the re-sealable individual package 2 may be re-sealed once the hygienic device 3 is removed from and/or placed back into the package 2. More specifically, the package 2 may be sealed on at least one side by a re-sealing member 11. Preferably, the re-sealing member 11 is positioned at least partially on the top portion of the package 2. In one embodiment herein, the re-sealing member is positioned on one of the halves of the internal surface of the package 2. In another embodiment, the re-sealing member 11 may be positioned at least partially on a package 2 external surface alone or in combination with the package 2 internal surface.

Of course, the re-sealing member may be positioned on both of the halves of the internal surface of the package 2 as well as positioned at least partially on the package external surfaces alone or in combination with the package internal surfaces. The re-sealing member 11 may be selected from the group consisting of re-fastenable tape, thermal bonds, pressure sensitive tapes, pressure sensitive glues, and combinations thereof.

In another embodiment herein, the individual package 2 further comprises a disruptive member 14 for opening the individual package 2. The disruptive member 14 is positioned adjacent to the top portion of the individual package 2. The disruptive member 14 extends partially along the top portion of the individual package 2. Preferably, the disruptive member 14 extends substantially along the top portion of the individual package 2. More specifically, the disruptive member 14 may comprise an opening device for opening the package 2. The opening device may comprise a pull-string, a line of weakness and/or perforations. Herein, the individual package may be, but is not necessarily re-sealable.

The preferable package 2 is substantially sealed about the longitudinal axis and sealed on at least three sides, at least one sealed side of the package being preferably re-sealable and two other sides being at least partially permanently sealed. The internal surface may comprise a first internal surface and a second internal surface facing toward the first internal surface.

The present invention will be explained in more detail based on the specific embodiments shown in the drawings. The following illustrates the present invention using a tampon as the hygienic device; but is not intended to exclude other hygienic devices.

The walls of the package can be of any desired thickness, commensurate with the intended use. Preferably, the walls are flexible and fluid-impermeable. Typically, the walls of package 2 have a thickness of from about 0.0127 mm (0.5 mil) to about 0.127 mm (5.0 mils). The package 2 may be made from plastic films that may be thermoplastic, nonwoven materials, collagen films, paper tissues, or laminates of tissue and a film, nonwoven material and a film, or any of the foregoing types of material with a coating thereon.

The increase in the tear strength when comparing the paper to the laminated material provides a stronger package that will not tear as easily as paper alone. The reduction in tear strength when comparing the film to the laminated paper and film enables the user to open the package with greater ease than if the package were made from the film alone. When the materials are laminated, the superior tear resistant properties of the film are compromised, yet the strength of the paper is significantly increased, providing an ideal package that is easily opened, yet strong enough to resist tearing from handling and transporting. The laminate is also quiet, in-use, emitting a "low rattle" noise rather than emitting a "scratchy," or "crinkly" noise, as in the case of many plastics. This also allows the package to be used discretely.

The laminated material, like a number of the other package materials identified above, also aids in heat sealing the package, provides a sanitary and moisture-free environment, and reduces noise associated with tearing paper when opening and carrying the package. The laminated material also produces a package that can be opened with or without a line of weakness.

In addition, numerous embodiments of the individual packages described herein are possible. For example, the package could be provided in other configurations while still performing the functions described herein. Further, the packaging materials described herein can be used with a variety of absorbent articles configured for the absorption of body fluids such as female or male incontinence products, tampons, or externally worn sanitary napkins where a hygienic environment is a paramount concern. For example, the adhesive on sanitary napkins and/or the wing adhesive of winged sanitary napkins can be covered by cover strips made of such materials. Additionally, a package that serves as a package for a sanitary napkin such as that described in U.S. Pat. No. 4,556,146 entitled "Individually Packaged Disposable Absorbent Article" which issued to Swanson et al. on Dec. 3, 1985 could be provided that is made of such a material.

As is specifically shown in FIGS. 1 and 2, the invention provides a re-sealable package 2 for a hygienic device 3 having a lateral x axis X and a longitudinal y axis Y. In addition, FIGS. 1 and 2 show a package 2 for a tampon device 3 said package having a body 4 comprising walls which surround and contain the device 3 within the body 4. The body 4 has a rupturable seal line 5 running along the lateral x axis X or the longitudinal y axis Y of at least one side of the body 4, and an opening member 7 situated on the seal line 5 and extending outward from the body 4, the member 7 being suitable for grasping with the fingers.

In addition, opening members 7 are preferably positioned along seal line 5 of the package 2 (FIG. 1). As is shown in FIG. 1, a user may grasp the opening members 7 to pull apart the package 2 to reveal only the grasping member 10 used for readily retrieving the intravaginal device 3 from the package 2 such that a user neither touches nor contaminates the absorbent member 9 with any part of her hand (FIG. 2). The opening member 7 or opening members 7 may be opened with a force in the range of about 30 to about 550 gms/cm2. Thus, when the package 2 is opened. The intravaginal device 3 is positioned within the package 2 such that only the grasping member 10, which is connected adjacent to the absorbent member 9 is directly accessible to the user.

Figure 6:
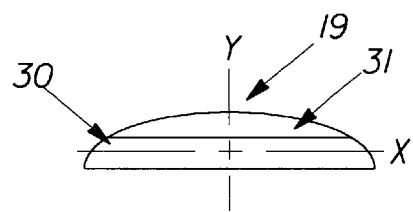
FIG. 6 is a side view of the tabs, offset in the lateral x direction.

The opening members 7 may be a tab 19 or a loop 29. In an alternative embodiment shown in FIG. 6 the package 2 is provided with tab 19. As shown in FIG. 6, tabs are off-set from each other in order to facilitate easy separation when opening. This can be achieved by off-setting the front tab 30 and back tab 31 by: height, length, phase (both tabs same size, but one is shifted longitudinally), and shape. The off-set should be between 2–6 mm.

As shown in FIG. 6, the tabs 19 may be offset from one another in the lateral x direction X or may be offset in the longitudinal y direction Y. The package 2 is opened by lifting the tab 19 and breaking the rupturable seal line 5 that are positioned along the upper portion of at least one side panel that is closest to the upper portion of the package 2 to create an opening for the wrapper. The present invention provides an easy and intuitive method of opening the package. The intuitive opening member 7 directs consumers to the grasping member 10 which results in optimal hygienic handling of the tampon applicators.

Whether re-sealable or non-resealable, the individual package 2 encloses the hygienic device 3 to provide a sanitary environment. The package 2 should at least partially enclose the hygienic device 3, and preferably completely enclose the hygienic device 3. The package 2 comprises at least one sheet of flexible material. The sheets may come in various sizes and shapes, such sizes and shapes not limiting the scope of the invention. The package 2 can be folded about or wrapped around the hygienic device 3 in any suitable manner. In one embodiment herein, the package 2 is preferably folded about or wrapped around the hygienic device 3.

Figure 3:
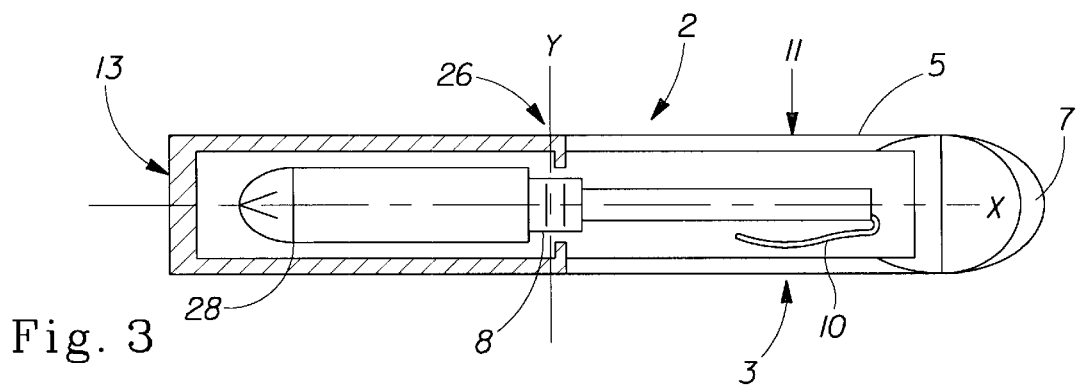
FIG. 3 is a side view of an embodiment of the individual package with offset tabs placed on the end and with the tampon residing therein.

After its use, the hygienic device 3 may be placed back into the package 2 and re-sealed for disposal purposes. At least one side of the re-sealable package 2 may be re-sealed once the intravaginal device 3 or any part of the intravaginal devices 3 is removed from and/or placed back into the package 2. The package 2 may be sealed on at least one side by an optional re-sealing member 11 (FIG. 3). Preferably, the re-sealing member 11 is positioned at least partially on the top of the package 2. In one embodiment herein, the re-sealing member 11 is positioned at least partially on the package 2 alone or in combination with the package 2.

Of course, the re-sealing member 11 may be positioned on at least partially on the package 2 external surfaces 11 alone or in combination with the package 2 internal surfaces 12. The re-sealing member 11 may be selected from the group consisting of re-fastenable tape, thermal bonds, pressure sensitive tapes, pressure sensitive glues and combinations thereof. In fact any suitable means for providing a re-sealing member 11 are readily foreseeable by one skilled in the art.

As is shown in FIGS. 1, 2, 3, 4, 5A, and 5B the package 2 further comprises permanent seals 13. By the term "permanent seals", it is meant herein seals that bind portions of the walls of the package 2 together in a substantially permanent and un-resealable manner. The permanent seals 13 generally extend partially along the sides of a package 2 in combination with the rupturable seal lines 5. If the permanent seals 13 extend only along a portion of the package sides, then those portions not permanently sealed will be sealed by one or more resealing members 11. The permanent seal 13 width ranges in the lateral x or the longitudinal y direction from about 1 mm to about 8 mm. Typically, permanent seals 13 herein are formed from heat seals, crimps, pressure seals and/or any other suitable sealing method known in the art. Any suitable sealing method known in the art may be used.

A permanent seal 13 may be placed on the same side of the opening member 7. Because the opening member 7 is placed parallel with the grasping member 10 and the permanent seal 13 is placed parallel with the absorbent member 9, the user can directly access the grasping member 10, but is unable to retrieve the absorbent member 9 after breaking the rupturable seal line 5. Thus, the user may only access the finger grip 8 or the pusher tube 27 because the permanent seals 13 do not allow the user to access the insertion member 9.

In another embodiment the package further comprises stop seals 26 placed adjacent to the rupturable seals and adjacent to the permanent seals 13 (FIGS. 1, 2, 3, 4, and 5B). The stop seals 26 provide additional reinforcement to only display the grasping member 10 after breaking the rupturable seal 5 of the package and to further ensure that the user will not tear the package into two pieces. Tearing the package into two pieces prevents the package from being reusable for disposal of the hygienic device 3. In addition, the stop seals 26 provide a signal to the user that the package 2 is opened wide enough to retrieve only the grasping member 10 of the applicator. The stop seals 26 also ensure proper usage for hygienic usage because the stop seals 26 are placed after the rupturable seal line 5 but before the permanent seals 13 which are placed parallel to the absorbent member 9.

Figure 4:
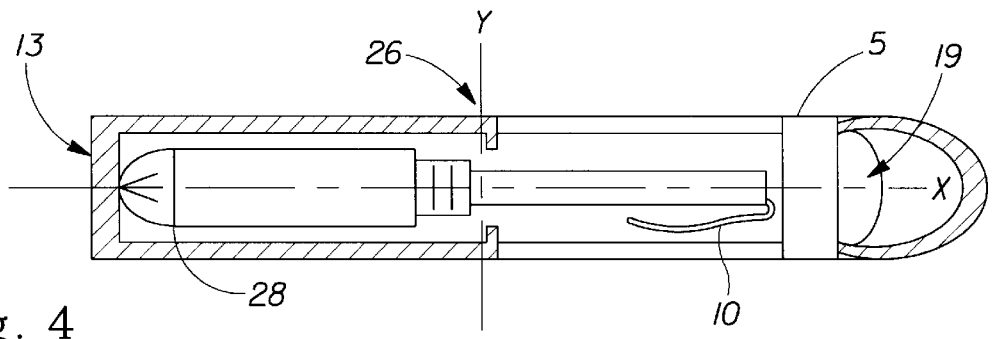
FIG. 4 is a side view of an embodiment of the individual package with offset tabs placed on the end and with the tampon residing therein.
Figure 7:
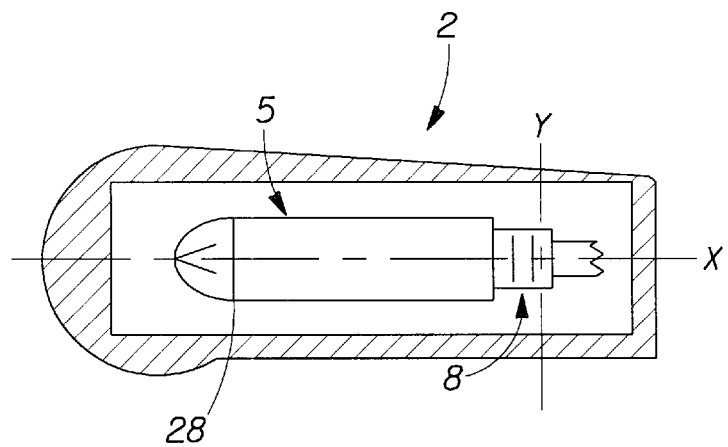
FIG. 7 is a side view of an individual package which has offset tabs from the center and hoods for disposal.
Figure 8:
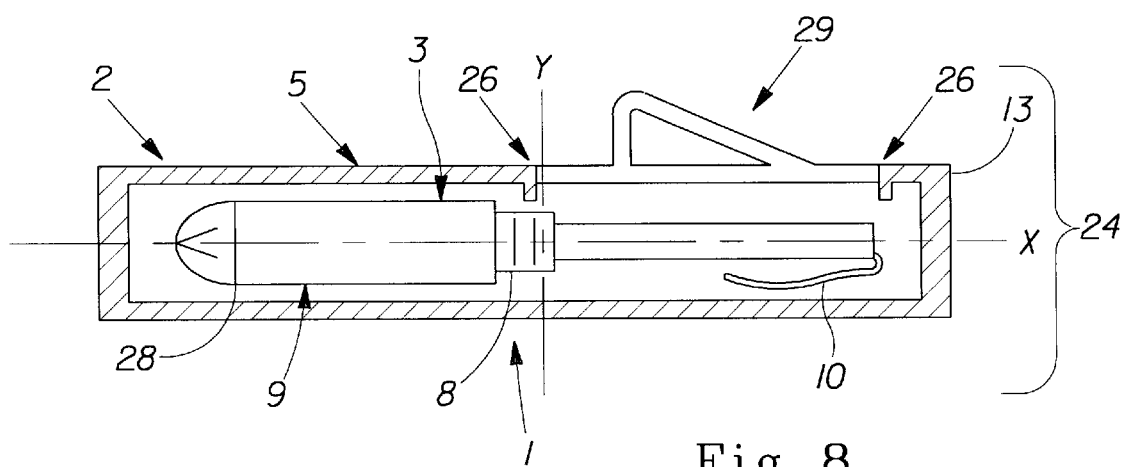
FIG. 8 is a cross sectional view of an embodiment of the individual package with loops placed on the side and with the tampon residing therein

The consumer may use the package for an applicator and/or a used tampon for disposal. The consumer may use the loose ends of the wrapper to secure the inserted used applicator by 1) tying the ends together (FIG. 2); 2) pressure sensitive adhesive; 3) Zipper in groove fastener (ZIP LOK FASTENER) (FIGS. 5A and 5B) such as a ZIP LOK Fastener; 4) VELCRO FASTENER (such as hook and loop); and 5) tucking the flaps or hood around the contained contents (FIG. 1, 4, and 7).

Figure 5A:
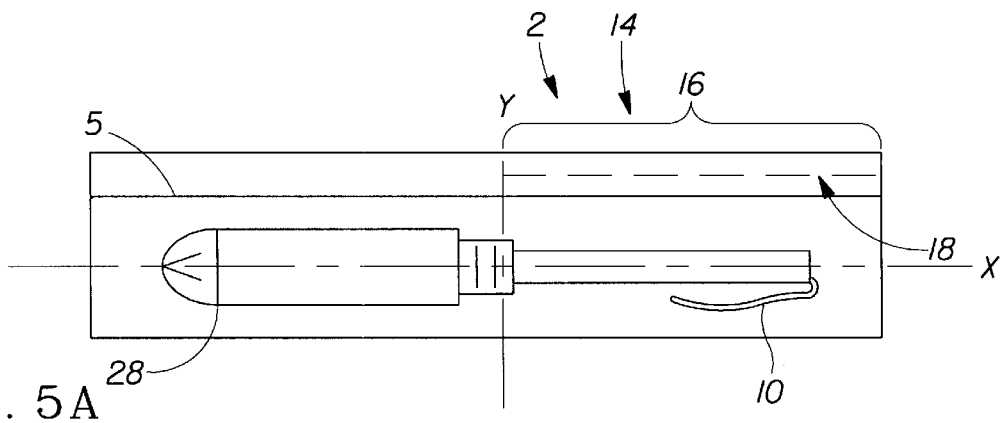
FIG. 5A is a side view of an alternative embodiment of the individual package with the tampon residing therein.
Figure 5B:
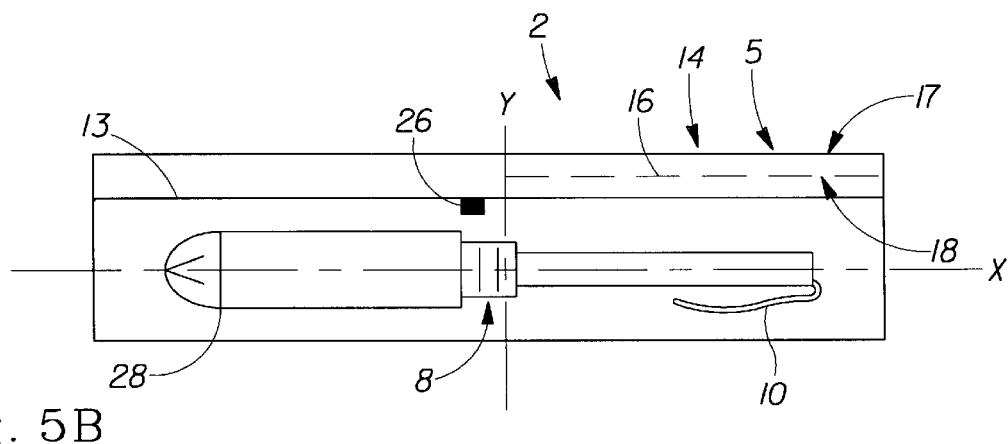
FIG. 5B is a side view of an alternative embodiment of the individual package with the tampon residing therein.

In another embodiment herein, the package 2 further comprises a disruptive member 14 or tear member 14 for opening the individual package 2 (FIGS. 5A–5B). In this context, the individual package 2 may be either re-sealable via the existence of one or more re-sealing members 11 placed within or on the package 2 or the package 2 may not be re-sealable at all. The disruptive member 14 is positioned within the top portion of the package 2 and includes a tear member 14 and a tear strip 16. The disruptive member 14 extends partially along the top portion of the package 2. Preferably, the disruptive member 14 extends substantially along the top portion of the package 2.

In practice, a user grasps the angled portion 17 of the tear member 14 and pulls the tear member 14 long the line of the tear strip 16, which is preferably a weakened and/or perforated portion. Once pulled, the tear member 14 should readily disrupt the tear strip 16 such that the package 2 is opened along the entire length of the tear strip 16. Once opened, the hygienic package 2 should reveal the grasping member 10 (FIGS. 5A and 5B).

The individual package 2 preferably comprises a seal line which constitutes a line of weakness which can be in the form of perforations 18 that are positioned along the upper portion of the package 2 (FIGS. 5A–5B). In addition to the perforations 18, the package must also contain a rupturable seal line 5 (FIG. 5B). The rupturable seal line 5 serves as a tamper-evident opening feature.

In other alternate embodiments, the line of weakness can be in the form of a score line, such as that made by laser scoring. The individual package 2 preferably also has a tear strip 16 or string that generally extends along and in the direction of the perforations 18. The individual package 2 is opened by using the tear string to break the perforations 18 along a significant portion of the periphery of the individual package 2. In addition to the seal line, the package must also contain a rupturable seal line 5. The rupturable seal line 5 serves as a tamper-evident opening feature.

The tampon 3 is of conventional shape and construction and should be of a suitable size and shape that allows at least a portion thereof to fit comfortably intravaginally. The intravaginal device 2 at least partially blocks, and more preferably completely blocks and intercepts the flow of menses, urine, and other bodily exudates from the wearer's vaginal orifice and urethra.

The intravaginal device 2 is preferably provided with sufficient absorbency to absorb and retain the exudates discharged from the wearer's body. The capacity of the product, however, is dependent at least partially upon the physical volume of the hygienic device 3, particularly the central absorbent portion thereof.

There are several ways to achieve a re-sealable wrapper. FIGS. 1, 2, 3, 4, 5A, 5B, and 8 highlight the different approaches. For instance in the "side tab wrapper" (FIGS. 2 and 3), as the 2 finger tabs are gripped and pulled, the wrapper peels open along the rupturable seal line 5 until the permanent seal 13 region is reached. The unused tampon is removed and the used tampon/applicator is put in and wrapped with the resealable wrapper.

To ensure a hygienic reseal, several closing mechanisms can be used. For instance, in FIG. 2, the used applicator is placed in the enclosed region (permanent seal region), and the excess, open wrap material wraps around the enclosed region much like a plastic sandwich bag. FIGS. 5A and 5B show a ziplock bag execution. FIGS. 1, 2, 4, and 7 show a "hood" that can wrap around a used applicator. Other reclosure features include incorporating a strip of glue, hammer material, velcro, etc.

One method of offsetting the tabs in the longitudinal y direction is to pre-crease the wrapper film/material; cut the wrapper material to length; place a permanent seal 13 on the tail end 24; (FIG. 1) place a permanent seal 13 on the longitudinal axis of the package 2; place a rupturable seal 5 on the longitudinal seal; die cut the tabs 19 to the final overall dimensions; cut the tab 19 off-set; insert the grasping portion of the tampon applicator first through the product head end 25 so that the grasping portion 8 is parallel to the rupturable seal line 5; and seal the head end 25 of the wrapper.

One method of offsetting the tabs in the lateral x direction is to die cut the tabs; pre-crease the wrapper material; cut the tabs 19 to length; place a permanent seal 13 on the tail end 24 and the longitudinal seal; put a rupturable seal 5 on the longitudinal seal; die cut the final overall dimensions; insert the grasping member 10 of the tampon applicator first through the product head end 25 so that the grasping member 10 is parallel to the rupturable seal line 5; and seal the head end 25 of the wrapper.

A suitable method for commercial production of the wrapper is to roll feed in flow wrap-type system; fold the wrapper on its longitudinal x axis; die cut the tabs; place a permanent seal on the tail end 24; place a permanent seal 13 on the longitudinal seal; place a rupturable seal 5 on the longitudinal seal; insert the grasping member 10 of the tampon applicator first through the product head end 25 so that the grasping member 10 is parallel to the rupturable seal line 5; seal the head end 25 of wrapper; die cut the final overall dimensions; and remove the trim.

As can be seen from the foregoing, the present invention has hygienic advantages. An advantage of the present invention is to provide an individual package for a hygienic device 3 that prevents the hand from directly contacting the part of the device that is worn interlabially, intravaginally, or worn near the hygienic space. The user's fingers are protected from touching the absorbent member 9 as the hygienic device 3 is removed from the package 2 because the permanent seal 13 is parallel to the absorbent member 9 while opening the package. Another advantage of the present invention is that it provides a protective covering for the hygienic device 3 during transport or storage of the product. Maintaining a hygienic environment for the hygienic device 3 before and during use is vital to prevent transferring unsanitary particles to the hygienic space and facilitates ease of removal from the package of a hygienic device 3 without the opportunity of contamination.

The present invention also presents disposal advantages. An advantage of the present invention is to provide a package for a sanitary tampon that has an additional function useful for the users of sanitary tampons even after it is opened. Furthermore, the integrity of the package is maintained because the permanent seals 13 are placed along the longitudinal x or y axis which prevents the user from tearing the package into two pieces. In this development portions of the wrapper seals are rupturable seal lines 5 or peelable, in that to access the product, the wrap is "peeled open" partially with, i.e., the wrapper has a directed opening 1) enough to expose only the grasping member 10 of the applicator (FIGS. 1, 2, 3, 4, 5 & 7). This allows the consumer a controlled hygienic opening, by only exposing the grasping member 10 of the applicator and leaving the absorbent member covered until removed. Because the permanent seal is left intact also allows the used tampon and/or applicator to be inserted into the "intact" portion of the wrapper. The consumer can then insert the used tampon and/or applicator into the "intact" portion of the wrapper, and then cover with the "peeled" portion of the wrapper for clean, hygienic disposal into a waste bin. The opened wrapper can be secured around the used applicator and/or tampon for ease of disposal.

What is claimed is:

1. A package comprising:
   a.) a body comprising walls having a longitudinal axis and a longitudinal center;
   b.) a rupturable seal line adjacent to a permanent seal running along the axis of at least one side of said body, said permanent seal has a greater tear force than said rupturable seal line;
   c.) a pair of opening members situated on said rupturable seal line and extending outward from said body, said members being suitable for grasping with the fingers; and
   d.) said opening members are situated opposite each other, on opposite sides of said rupturable seal line, and along the longitudinal axis of said body.

2. A package according to claim 1 wherein said opening members are laterally displaced from the longitudinal center of said body.

3. A package according to claim 1 wherein said seal line of said package may be re-sealed after opening.

4. A kit, comprising:
   a.) a hygienic device, comprising a grasping member and absorbent member; and
   b.) a package, comprising
      i.) a body with walls having a longitudinal axis and a longitudinal center;
      ii.) a rupturable seal line adjacent to a permanent seal running along one side of said body, said permanent seal line has a greater tear force than said rupturable seal line;
      iii.) a pair of opening members situated on said rupturable seal line extending outward from the body of said package said members being suitable for grasping with the fingers; and said opening members are situated opposite each other, on opposite sides of said rupturable seal line, and along the longitudinal axis of said body; wherein
         said hygienic device being situated within the body of said package such that the grasping member of said device is first presented to the user when the rupturable seal line is ruptured and the permanent seal is not broken.

5. A kit according to claim 4 wherein the opening member is a tab.

6. A kit according to claim 4 wherein the opening member is a loop.

7. A kit according to claim 4 wherein the hygienic device is a tampon in combination with its applicator.

* * * * *